United States Patent [19]

Uphues et al.

[11] Patent Number: 5,925,747
[45] Date of Patent: Jul. 20, 1999

[54] PUMPABLE WATER-CONTAINING SURFACTANT CONCENTRATES

[75] Inventors: Guenter Uphues; Joerg Kahre, both of Monheim; Ansgar Behler, Bottrop; Peter Neumann, Duesseldorf; Hermann Hensen, Haan; Werner Seipel, Hilden; Holger Tesmann, Juechen, all of Germany

[73] Assignee: Henkel Kommanditgesellschaft auf Aktien, Duesseldorf, Germany

[21] Appl. No.: 08/817,478

[22] PCT Filed: Sep. 25, 1995

[86] PCT No.: PCT/EP95/03797

§ 371 Date: Apr. 4, 1997

§ 102(e) Date: Apr. 4, 1997

[87] PCT Pub. No.: WO96/10558

PCT Pub. Date: Apr. 11, 1996

[30] Foreign Application Priority Data

Oct. 4, 1994 [DE] Germany .................... 44 35 495

[51] Int. Cl.⁶ ............... C07G 3/00; C07H 15/00; C07H 1/00
[52] U.S. Cl. .............. 536/18.5; 536/4.1; 536/123.1; 536/124; 514/25
[58] Field of Search .................... 536/18.5, 4.1, 536/123.1, 124; 514/25

[56] References Cited

U.S. PATENT DOCUMENTS

| | | | |
|---|---|---|---|
| 4,668,422 | 5/1987 | Malik et al. | 252/174.2 |
| 5,281,749 | 1/1994 | Uphues et al. | 562/40 |
| 5,286,406 | 2/1994 | Scholz et al. | 252/174.17 |
| 5,374,716 | 12/1994 | Biermann et al. | 536/18.6 |
| 5,389,282 | 2/1995 | Saijo et al. | 252/174.17 |
| 5,576,425 | 11/1996 | Hill et al. | 536/18.6 |
| 5,578,560 | 11/1996 | Giesen et al. | 510/237 |

FOREIGN PATENT DOCUMENTS

| | | |
|---|---|---|
| 0 075 994 | 4/1983 | European Pat. Off. . |
| 0 250 181 | 12/1987 | European Pat. Off. . |
| 0 301 298 | 2/1989 | European Pat. Off. . |
| 0 341 071 | 11/1989 | European Pat. Off. . |
| 0 353 580 | 2/1990 | European Pat. Off. . |
| 0 453 238 | 10/1991 | European Pat. Off. . |
| 0 508 507 | 10/1992 | European Pat. Off. . |
| 0 510 870 | 10/1992 | European Pat. Off. . |
| 0 513 138 | 11/1992 | European Pat. Off. . |
| 39 39 264 | 5/1991 | Germany . |
| 42 34 487 | 4/1994 | Germany . |
| 43 05 083 | 8/1994 | Germany . |
| 43 11 114 | 10/1994 | Germany . |
| 2-187499 | 7/1990 | Japan . |
| WO 90/03977 | 4/1990 | WIPO . |
| WO 91/11506 | 8/1991 | WIPO . |
| WO 91/14761 | 10/1991 | WIPO . |
| WO 93/25650 | 12/1993 | WIPO . |
| WO 95/14658 | 6/1995 | WIPO . |

OTHER PUBLICATIONS

Skin Care Forum, (1992) p. 1.
Seifen–Öle–Fette–Washse, 118, (1992) p. 894.
Seifen–Öle–Fette–Washse, 118, (1992) p. 905.
Rivista Italiana, 56, (1974) p. 567.
"Kosmetische Färbemittel " der Farbstoffkommission der Deutschen Forschungsgemeinschaft, published by Verlag Chemie, Weinheim, 1984, pp. 81 to 106.

*Primary Examiner*—James O. Wilson
*Assistant Examiner*—Everett White
*Attorney, Agent, or Firm*—Ernest G. Szoke; Wayne C. Jaeschke; Henry E. Millson, Jr.

[57] ABSTRACT

Pumpable water-containing surfactant concentrates with a solids content of 30 to 60% by weight containing (a) alkyl and/or alkenyl oligoglycosides and (b) amphoteric or zwitterionic surfactants in a ratio by weight of 10:90 to 90:10, based on the solids content; processes for their preparation and their use in the production of surface-active formulations.

8 Claims, No Drawings

PUMPABLE WATER-CONTAINING SURFACTANT CONCENTRATES

This application is a 371 of PCT/EP95/03797, filed Sep. 25, 1995.

BACKGROUND OF THE INVENTION

1. Field of the Invention

This invention relates to pumpable water-containing surfactant concentrates containing alkyl and/or alkenyl oligoglycosides and betaine surfactants, to a process for their production and to their use for the production of surface-active formulations.

2. Statement of Related Art

Alkyl oligoglycosides, more particularly alkyl oligoglucosides, are nonionic surfactants which are acquiring increasing significance by virtue of their excellent detergent properties and their high ecotoxicological compatibility. The production and use of these substances have been described just recently in a number of synoptic articles, of which the articles by H. Hensen in Skin Care Forum, 1, (October 1992), D. Balzer and N. Ripke in Seifen-Öle-Fette-Wachse 118, 894 (1992) and B. Brancq in Seifen-Öle-Fette-Wachse 118 905 (1992) are cited as examples.

In some respects, however, the use of alkyl oligoglucosides is attended by problems. For example, it is not possible to produce pumpable water-containing concentrates with a solids content above 40% by weight without the sugar component undergoing partial decomposition in the course of the concentration process. The glycosides share this property with most anionic surfactants which form a viscous gel phase above an active substance content of around 35% by weight. In addition, alkyl oligoglucosides tend to crystallize during storage at low temperatures which significantly complicates their subsequent use.

The use of alkyl glucosides together with amphoteric or zwitterionic surfactants of the betaine type in surface-active formulations is known in principle from the prior art.

Mixtures of—albeit short-chain—alkyl glucosides and alkyl amido-betaines or imidazolinium betaines were disclosed for the first time in an article by G. Proserpio et al. in Rivista Italiana 56, 567 (1974). EP-A 0 075 994 (Procter & Gamble) discloses combinations of alkyl glucosides with amine oxides, unsaturated soaps, water-soluble builders and selected anionic surfactants. In addition, the mixtures may contain amphoteric surfactants, for example betaines of the 6-(N-dodecylbenzyl-N,N-dimethylammonium)-hexanoate type. Liquid soaps and foam baths containing alkyl glucosides, betaines and amine oxides are known from U.S. Pat. No. 4,668,422 (Henkel Corp.). EP-A 0 250 181 (Helene Curtis) relates to liquid detergents containing alkyl glucosides, anionic surfactants and selected amphoteric surfactants of betaine structure. EP-A 0 341 071 (Unilever) discloses surfactant combinations containing alkyl glucosides, alkyl sulfates, betaines and/or amine oxides and optionally alkanolamides. Manual dishwashing detergents containing alkyl glucosides, fatty alcohol sulfates, fatty alcohol ether sulfates and betaines are known from EP-A 0 513 138, DE-A1 4 234 487 and DE-A1 4 311 114 (all Henkel KGaA). EP-A 0 453 238 (Unilever) describes mild shampoos based on alkyl glucosides, anionic surfactants and betaines. Finally, EP-A 0 508 507 (Berol Nobel) relates to liquid detergents containing alkyl glucosides, anionic surfactants and selected amphoteric surfactants of betaine structure. However, these documents all relate to dilute water-containing surfactant mixtures or formulations and not to concentrates.

In EP-A2 0 353 580 (Th. Goldschmidt), it is proposed to prepare concentrated, flowable, water-containing solutions of betaines optionally containing lower aliphatic alcohols by carrying out the quaternization reaction in aqueous or aqueous/alcoholic solution in the presence of nonionic surfactants in such a quantity that the resulting solution has a nonionic surfactant content of, preferably, 3 to 20% by weight. Suitable nonionic surfactants for this purpose are, above all, fatty acid polyethylene oxide esters. In addition, it is known from DE-A1 4 305 083 (Henkel KGaA) that the quaternization of amines can be carried out in the absence of water and organic solvents, even in the presence of fatty alcohol polyglycol ethers.

There is a need in the market for concentrated surfactant mixtures based on alkyl and/or alkenyl oligoglucosides which are flowable and pumpable, despite a solids content above 30% by weight and preferably from around 40 to 50% by weight, and show a significantly reduced tendency towards crystallization, i.e. improved stability in storage. Since surfactant compounds of the type in question are mainly used in the cosmetics field, skin-cosmetic or father dermatological compatibility is also of paramount importance.

Surfactant concentrates are a particularly convenient commercial formulation for manufacturers and users alike because they have been minimized in regard to their water content and hence incur lower transportation and storage costs. Nevertheless, it is desirable that surfactant concentrates should have a sufficiently high viscosity for use in the end products, which are of course heavily diluted and have a solids content of 20 to 30% by weight, and should be readily thickenable using known additives.

Accordingly, the complex problem addressed by the present invention was to provide pumpable water-containing surfactant concentrates with high dermatological compatibility based on alkyl and/or alkenyl oligoglycosides which would be distinguished by high stability in storage, would have a Brookfield viscosity of at most 10,000 mpa.s and a solids content of 30 to 50% by weight and would readily lend themselves to thickening to a viscosity of at least 2,000 mPa.s on incorporation in cosmetic formulations with a water content of at least 50% by weight.

DESCRIPTION OF THE INVENTION

The present invention relates to pumpable water-containing surfactant concentrates with a solids content of 30 to 60% by weight and preferably 40 to 50% by weight containing a) alkyl and/or alkenyl oligoglycosides and
(b) amphoteric or zwitterionic surfactants in a ratio by weight of 10:90 to 90:10, preferably in a ratio by weight of 20:80 to 80:20 and more preferably in a ratio by weight of 40:60 to 60:40, based on the solids content of the concentrates.

It has surprisingly been found that the surfactant concentrates according to the invention show excellent skin-cosmetic compatibility, good foaming properties, even when mixed with other surfactants, such as fatty alcohol ether sulfates in particular, and very good stability in storage, even at low temperatures. In particular, the formation of crystals, as known from water-containing alkyl glucoside pastes, is reliably avoided. The present invention also includes the observation that the surfactant concentrates have the necessarily low viscosity of less than 10,000 mPa.s and preferably 3,000 to 7,500 mpa.s (as determined by the Brookfield method), but can readily be thickened to a viscosity of at least 2,000 mpa.s in dilute water-containing formulations.

The present invention also relates to a process for the production of pumpable, water-containing surfactant concentrates in which secondary or tertiary amines are reacted with alkylating agents in known manner in the presence of alkyl and/or alkenyl oligoglycosides. It is pointed out in this connection that the production of the surfactant concentrates according to the invention with the required solids content is not readily possible by other methods, for example by mixing the water-containing individual components or by introducing powder-form alkyl glucosides into aqueous betaine pastes.

Amines

Suitable amine components are secondary and, in particular, tertiary amines. Suitable starting materials are, for example, dialkylamines and preferably trialkylamines corresponding to formula (I):

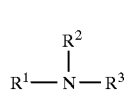

in which $R^1$ represents alkyl and/or alkenyl radicals containing 6 to 22 carbon atoms, $R^2$ represents hydrogen or alkyl radicals containing 1 to 4 carbon atoms and $R^3$ represents alkyl radicals containing 1 to 4 carbon atoms.

Typical examples are hexyl methylamine, hexyl dimethylamine, octyl dimethylamine, decyl dimethylamine, dodecyl methylamine, dodecyl dimethylamine, dodecylethyl methylamine, $C_{12/14}$ cocoalkyl dimethylamine, myristyl dimethylamine, cetyl dimethylamine, stearyl dimethylamine, stearyl ethyl methylamine, oleyl dimethylamine, $C_{16/18}$ tallow alkyl dimethylamine and technical mixtures thereof.

Other suitable starting materials are amidoamines corresponding to formula (II):

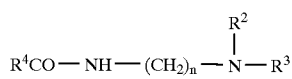

in which $R^4CO$ is an aliphatic acyl radical containing 6 to 22 carbon atoms and 0 or 1 to 3 double bonds, n is a number of 1 to 3 and $R^2$ and $R^3$ are as defined above.

Amidoamines are known compounds which may be obtained by the relevant methods of preparative chemistry. One process for their production comprises, for example, amidating fatty acids with diamines. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethylamine, N,N-dimethylaminopropylamine, N,N-diethylaminoethylamine and N,N-diethylaminopropylamine. It is preferred to use $C_{8/18}$ coconut oil fatty acid N,N-dimethylaminopropylamide.

Other suitable amines are imidazolines corresponding to formula (III):

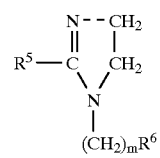

in which $R^5$ is an alkyl radical containing 5 to 21 carbon atoms, $R^6$ is a hydroxyl group, an $OCOR^5$ or $NHCOR^5$ group and m=2 or 3.

These compounds are also known and may be obtained, for example, by cyclizing condensation of 1 or 2 moles of fatty acid with polyfunctional amines such as, for example, aminoethyl ethanolamine (AEEA) or diethylenetriamine.

Typical examples are condensation products of the above-mentioned fatty acids with AEEA, preferably imidazolines based on lauric acid or $C_{12/14}$ coconut oil fatty acid.

Alkyl and/or alkenyl oligoglycosides

Alkyl and/or alkenyl oligoglycosides are known substances and correspond to formula (IV):

$$R^7O-[G]_p \qquad (IV)$$

in which $R^7$ is an alkyl and/or alkenyl radical containing 10 to 22 carbon atoms, G is a sugar unit containing 5 or 6 carbon atoms and p is a number of 1 to 10. Alkyl and/or alkenyl oligoglycosides may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (IV) indicates the degree of oligomerization (DP degree), i.e. the distribution of mono- and oligoglycosides, and is a number of I to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.5 are preferred from the applicational point of view.

The alkyl or alkenyl radical $R^7$ may be derived from primary alcohols containing 10 to 22 and preferably 12 to 16 carbon atoms. Typical examples are caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and the technical mixtures thereof obtained, for example, in the hydrogenation of technical fatty acid methyl esters or in the hydrogenation of aldehydes from Roelen's oxosynthesis. Alkyl oligoglucosides based on hydrogenated $C_{12/14}$ cocoalcohol with a DP of 1 to 3 are preferred.

The amines and the glycosides are normally used in a ratio by weight of 10:90 to 90:10, preferably in a ratio by weight of 20:80 to 80:20 and more preferably in a ratio by weight of 40:60 to 60:40.

Alkylating agents

Halocarboxylic acids and alkali metal salts or esters thereof may be used as the alkylating agents. It is preferred to use sodium chloroacetate by virtue of its ready availability. The amines and the halocarboxylic acids or their salts may be used in a molar ratio of 1:1.0 to 1:2.5 and preferably in a molar ratio of 1:1 to 1:2.0. A high ratio is particularly advantageous when imidazolines are used as the amines.

Quaternization

The quaternization or betainization of the amines may be carried out in known manner. It is advisable to carry out the reaction in such a quantity of water as solvent that the surfactant concentrates obtained have a solids content of 30 to 50% by weight and preferably 43 to 48% by weight. Instead of water, fatty alcohol polyglycol ethers, ethoxylated partial glycerides, lower alkyl glycosides containing 4 to 8 carbon atoms in the alkyl radical and the like may be used. Mixtures of water and the solvents mentioned may also be used as the solvent. The alkylation reaction is normally carried out at temperatures in the range from 70 to 98° C. and is complete after 1 to 10 hours and preferably 2 to 5 hours.

To ensure that the alkylating agent reacts off completely, it has proved to be of advantage to carry out the reaction at a pH value in the range from 6 to 10 and preferably in the range from 7 to 8.5. Another way of minimizing the residual content of alkylating agent is to add a certain excess of aminoacids, more particularly glycine, to the reaction mixture on completion of the alkylation reaction, as described in DE-A1 3 939 264 (Henkel).

In one preferred embodiment of the invention, the reaction products obtained after the alkylation reaction are subjected to a pressure aftertreatment at temperatures in the range from 80 to 140° C., under pressures of 1 to 10 bar and at pH values of 8 to 13. This leads to a minimization of the residual content of chloroacetic acids.

Commercial Applications

The water-containing surfactant concentrates according to the invention have a solids content of 30 to 50% by weight. They are stable in storage, do not show any tendency to crystallize, have a viscosity of less than 10,000 mPa.s and, accordingly, are pumpable. In dilute water-containing formulations, they can readily be rethickened and show excellent skin-cosmetic compatibility. If the surfactant concentrates already contain a thickener, there may often be no need at all to add other thickeners, preferably narrow-range fatty alcohol polyglycol ethers, to the cosmetic formulations because the required viscosity is automatically established. Accordingly, the present invention also relates to the use of the surfactant concentrates according to the invention for the production of surface-active formulations, such as for example dishwashing detergents and, in particular, skin-care and hair-care formulations.

Skin-care and hair-care formulations

The skin-care and hair-care formulations may contain further surfactants compatible with the other ingredients in small quantities. Typical examples are fatty alcohol polyglycol ethersulfates, monoglyceride sulfates, ether carboxylic acids, fatty acid isethionates, fatty acid sarcosinates, fatty acid taurides, acyl glutamates and/or protein hydrolyzates or condensates thereof with fatty acids of animal or preferably vegetable origin.

In addition to the surfactants already mentioned, skin-care formulations, such as creams, lotions and the like, generally contain oils, emulsifiers, fats and waxes, stabilizers and also superfatting agents, thickeners, biogenic agents, film formers, preservatives, dyes and fragrances.

In addition to the surfactants already mentioned, hair-care formulations, such as for example hair shampoos, hair lotions, foam baths and the like, may contain emulsifiers, superfatting agents, thickeners, biogenic agents, film formers, preservatives, dyes and fragrances as further auxiliaries and additives.

Suitable oil components are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more particularly 2-ethylhexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes, Guerbet carbonates and/or dialkyl ethers.

Suitable emulsifiers are both known w/o and o/w emulsifiers such as, for example, hydrogenated and ethoxylated castor oil, polyglycerol fatty acid esters or polyglycerol polyricinoleates.

Typical examples of fats are glycerides while suitable waxes include inter alia beeswax, paraffin wax or microwaxes, optionally in combination with hydrophilic waxes, for example cetostearyl alcohol.

Suitable stabilizers are metal salts of fatty acids such as, for example, magnesium, aluminium and/or zinc stearate.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, narrow-range fatty alcohol ethoxylates or alkyl oligoglucosides and electrolytes, such as sodium chloride and ammonium chloride.

In the context of the invention, biogenic agents are, for example, plant extracts and vitamin complexes.

Typical film formers are, for example, chitosan, microcrystalline chitosan or quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and also fatty acid monoglycol esters.

The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total percentage content of auxiliaries and additives may be from 1 to 50% by weight and is preferably from 5 to 40% by weight while the non-aqueous component ("active substance content") may amount to between 20 and 80% by weight and preferably to between 30 and 70% by weight, based on the formulation. The formulations may be produced in known manner, i.e. for example by hot, cold, hot-hot/cold or PIT emulsification. These are all purely mechanical processes in which no chemical reaction takes place.

The following Examples are intended to illustrate the invention without limiting it in any way.

EXAMPLES

Production Examples

Example H1:

$C_{8/18}$ coconut oil fatty acid amidopropyl-N,N-dimethylaminobetaine/$C_{12/14}$ alkyl oligoglucoside ("compound A").

In a 2 liter four-necked flask equipped with a stirrer, thermometer, dropping funnel and pH electrode, 44.6 g (0.375 mole) of sodium chloroacetate (96% by weight) were homogenized at 40° C. together with 145.3 g of water and 1204.2 g of $C_{12/14}$ cocoalkyl oligoglucoside (Plantaren® APG 600 CS UP, Henkel KGaA, Düsseldorf (FRG); 50% by weight aqueous paste). 102.7 g (0.33 mole) of hydrogenated $C_{8/18}$ coconut oil fatty acid amidopropyl-N,N-dimethylamine were then added and the mixture was kept at 90° C. The initial pH value was around 11 due to the alkalization of the glycoside, falling to 9.7 during the three-hour reaction. By this time, the amidoamine had completely reacted off. A pumpable liquid with the following composition was obtained:

7.7% by weight betaine
40.2% by weight alkyl oligoglucoside
1.3% by weight sodium chloride
50.4% by weight water
0.1 % by weight sodium chloroacetate The crude product was transferred to an autoclave in which 50% by weight sodium hydroxide solution was added to it in such a quantity that a pH value of 11.5 was obtained, based on a 10% by weight dilution of the product. The mixture was then aftertreated for 60 minutes at a temperature of 120° C. and under an autogenous pressure of 2 bar, the residual content of sodium chloroacetate being minimized to a value of <5 ppm.

Example H1:

$C_{12/18}$ cocoalkyl-N,N-dimethylaminobetaine/$C_{12/14}$-alkyl oligoglucoside ("compound B").

As in Example H1, 85.2 g (0.72 mole) of sodium chloroacetate, 235.0 g of water and 1050 g of $C_{12/14}$ coco-oligoglucoside were mixed with 139.7 g (0.63 mole) of cocodimethylamine and reacted at 90° C. The pH value was initially 10.4, falling to 8.5 over a reaction time of 2.5 h. By this time, the residual amine content was 0.3% by weight. A free-flowing liquid with the following composition was obtained:

11.7% by weight betaine
35.0% by weight alkyl oligoglucoside
2.8% by weight sodium chloride
48.3% by weight water
0.3% by weight sodium chloroacetate The sodium chloroacetate content was reduced to 9 ppm by an aftertreatment as in Example H1.

II. Testing of the concentrates

The viscosity of the following mixtures was determined by the Brookfield method (23° C., spindle 2, 200 r.p.m.). The stability of the mixtures was visually evaluated after storage for 4 weeks at 5° C. The symbols used have the following meanings:

+++=clear solution, no crystallization
++=some crystallization
+=distinct crystallization
−=parts of the solution completely crystallized
*=hazy product, unstable, phase separation The compositions and the viscosity and stability data are set out in Tables 1 and 2. The figures relating to the compositions of the mixtures (in % by weight) are based on the solids content of the components. All the mixtures were used with a water content of 55% by weight (pH value 5.3).

An explanation of the trade names is given in Table 4.

TABLES 1 and 2

| Components | 1 | 2 | 3 | 4 | 5 |
|---|---|---|---|---|---|
| Compound A | 96.0 | — | 97.0 | 97.5 | — |
| Compound B | — | 97.0 | — | — | 96.0 |
| Arlypon ® F | 1.0 | 1.0 | 0.5 | — | 1.5 |
| Preservative | 0.1 | 0.1 | 0.1 | 0.1 | 0.1 |
| Lactic acid 85% | 2.9 | 1.9 | 2.4 | 2.4 | 2.4 |
| Viscosity [mPas] | 7000 | 4900 | 4250 | 3700 | 4900 |
| Stability | +++ | +++ | +++ | +++ | +++ |

| Components | C1 | C2 | C3 | C4 | C5 |
|---|---|---|---|---|---|
| Plantaren ® 600 | 50.0 | — | — | 50.0 | 50.0 |
| Plantaren ® 2000 | — | 50.0 | — | — | — |
| Texapon ® SB 3 | 46.0 | 46.0 | 50.0 | 40.0 | 6.0 |
| Dehyton ® K | — | — | 46.0 | 6.0 | 40.0 |
| Arlypon ® F | 1.0 | 1.0 | 1.0 | 1.0 | 1.0 |
| Preservative | 0.1 | 0.1 | 0.1 | 0.1 | 0.1 |
| Lactic acid 85% | 2.9 | 2.9 | 2.9 | 2.9 | 2.9 |
| Viscosity [mPas] | 14000 | 12000 | 5600 | 9400 | 9400 |
| Stability | — | — | * | ++ | + |

III. Testing of the dilute ready-to-use formulations

Concentrates 1 to 5 according to the invention and comparison mixtures C1 to C5 were used in the formulation of a dilute cosmetic skin lotion:

| Surfactant concentrate (water-free) | 10.0% by weight |
|---|---|
| Dehyton ® G | 5.0% by weight |
| Lamepon ® S | 2.5% by weight |
| Euperlan ® PK 900 | 1.5% by weight |
| Cetiol ® HE | 1.0% by weight |
| Lamesoft ® LMG | 2.5% by weight |
| Dye | 1.0% by weight |
| Preservative | 0.1% by weight |
| Water | 76.4% by weight |

The results are set out in Table 3

TABLE 3

Viscosity in the in-use concentration

| Ex. | pH Value | Viscosity mPas | Viscosity on addition of 1% by weight Arlypon ® F mPas |
|---|---|---|---|
| 1 | 5.3 | 4400 | |
| 2 | 5.2 | 4100 | |
| 3 | 5.3 | 4300 | |
| 4 | 5.4 | 4350 | |
| 5 | 5.3 | 4300 | |
| C1 | 5.3 | 980 | 1200 |
| C2 | 5.3 | 940 | 1100 |
| C3 | 5.3 | 1050 | 1200 |
| C4 | 5.3 | 990 | 1100 |
| C5 | 5.4 | 960 | 1100 |

TABLE 4

Explanation of the trade names

| Trade Name | CTFA Registration |
| --- | --- |
| Arlypon ® F | Laureth-2 |
| Cetiol ® HE | PEG-7 Glyceryl Cocoate |
| Dehyton ® G | Cocoamphodiacetate |
| Dehyton ® K | Cocamidopropyl Betaine |
| Euperlan ® PK 900 | PEG-3 Distearate (and) Sodium Laureth Sulfate |
| Lamepon ® S | Potassium-Cocoyl Hydrolyzed Collagen |
| Lamesoft ® LMG | Glyceryl Laurate (and) Potassium-Cocoyl Hydrolyzed Collagen |
| Plantaren ® 600 | Lauryl Polyglucose |
| Plantaren ® 2000 | Decyl Polyglucose |
| Texapon ® SB3 | Disodium Laureth Sulfosuccinate |

We claim:

1. A process for the production of a pumpable aqueous surfactant concentrate consisting of water, at least one alkyl or alkenyl oligoglycoside and at least one amphoteric or zwitterionic surfactant comprising reacting at least one secondary or tertiary amine with an alkylating agent in the presence of water and at least one alkyl or alkenyl oligoglycoside to form at least one amaphoteric or zwitterionic surfactant, wherein the concentrate has a solids content of from about 30 to about 60% by weight.

2. The process of claim 1 wherein the at least one secondary or tertiary amine is selected from the group consisting of (i) a secondary or tertiary amine corresponding to formula (I):

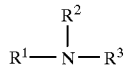

in which $R^1$ represents an alkyl or alkenyl radical containing from 6 to 22 carbon atoms, $R^2$ represents hydrogen or an alkyl radical containing 1 to 4 carbon atoms, and $R^3$ represents an alkyl radical containing 1 to 4 carbon atoms;

(ii) an amidoamine corresponding to formula (II):

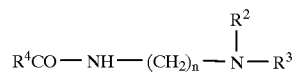

in which $R^4CO$ is an aliphatic acyl radical containing 6 to 22 carbon atoms and 0 or 1 to 3 double bonds, n is 0 or a number of 1 to 3 and $R^2$ and $R^3$ are as defined above; and (iii) an imidazoline corresponding to formula (III):

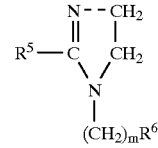

in which $R^5$ is an alkyl radical containing 5 to 21 carbon atoms, $R^6$ is a hydroxyl group, an $OCOR^5$ or $NHCOR^5$ group, and m=2 or 3.

3. The process of claim 2 wherein the at least one alkyl or alkenyl oligoglycoside has the formula (IV):

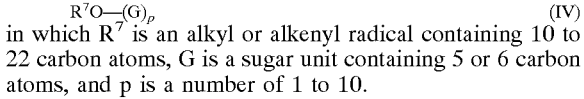

in which $R^7$ is an alkyl or alkenyl radical containing 10 to 22 carbon atoms, G is a sugar unit containing 5 or 6 carbon atoms, and p is a number of 1 to 10.

4. The process of claim 3 wherein the alkylating agent is a halocarboxylic acid or an alkali metal salt or ester thereof.

5. The process of claim 4 wherein said amine and said oligoglycoside are present in a ratio by weight of from about 20:80 to about 80:20.

6. The process of claim 5 wherein the reaction is carried out at a temperature in the range of from about 70 to about 98° C.

7. The process of claim 6 wherein the reaction is carried out over a period of from about 1 to about 10 hours at a pH of from about 6 to about 10.

8. The process of claim 5 wherein the reaction is followed by a pressure aftertreatment carried out at a temperature of from about 80 to about 140° C. and a pressure of from about 1 to about 10 bar and at a pH of from about 8 to about 13.

* * * * *